United States Patent
Asaoka et al.

(10) Patent No.: US 6,692,729 B1
(45) Date of Patent: Feb. 17, 2004

(54) COSMETIC RESIN COMPOSITION AND COSMETIC USING THE SAME

(75) Inventors: Seiji Asaoka, Suita (JP); Takahiro Sakurai, Ogaki (JP); Katsuya Koyama, Itami (JP); Toshitaka Tsuzuki, Mino (JP); Tomohiro Hashimoto, Kawanishi (JP)

(73) Assignee: National Startch and Chemical Investment Holding Corporation, New Castle, DE (US)

( * ) Notice: Subject to any disclaimer, the term of this patent is extended or adjusted under 35 U.S.C. 154(b) by 0 days.

(21) Appl. No.: 10/009,958
(22) PCT Filed: Apr. 13, 2000
(86) PCT No.: PCT/US00/09956
§ 371 (c)(1),
(2), (4) Date: May 29, 2002
(87) PCT Pub. No.: WO02/05621
PCT Pub. Date: Jan. 24, 2002

(51) Int. Cl.$^7$ .................................................. A61K 7/11
(52) U.S. Cl. ...................... 424/70.1; 424/70.1; 424/401
(58) Field of Search ............................. 424/401, 70.1, 424/70.11

(56) References Cited

U.S. PATENT DOCUMENTS

| | | |
|---|---|---|
| 4,777,224 A | 10/1988 | Gorzynski et al. |
| 5,626,840 A | 5/1997 | Thomaides et al. |
| 5,759,666 A | 6/1998 | Carlson et al. |

*Primary Examiner*—Jyothsna Venkat
(74) *Attorney, Agent, or Firm*—Karen G. Kaiser

(57) ABSTRACT

A cosmetic resin composition consisting essentially of an amphoteric urethane resin having a carboxyl group and a tertiary amino group in one molecule there of, the amphoteric urethane resin having a structural unit derived from an ethylene oxide in its structure.

7 Claims, No Drawings

COSMETIC RESIN COMPOSITION AND COSMETIC USING THE SAME

This application is a 371 of PCT/US/00/09950 filed on Apr. 13, 2000.

The present invention relates to a cosmetic resin composition consisting essentially of amphoteric urethane resin and a cosmetic using such a resin composition, and particularly, to a cosmetic resin composition used for a skin care product a hair care product and the like as a hair fixative, a film forming agent, a conditioning agent, a viscosity controlling agent and the like, and a cosmetic using the same.

Conventionally, a cationic acrylic resin, an anionic acrylic resin, an amphoteric or an ionic/cationic acrylic resin, a nonionic polyvinyl pyrrolidone resin and the like are used as a base resin of a hair fixative. When such a resin is used as a base resin, hair is set stiff, resulting in a good setting property (stiffness), but feel and combability are inferior and also flaking may occur. On the other hand, when feel and combability come first, not only setting property becomes insufficient, but also problems such as stickiness and the like may occur. Thus, it is difficult for the conventional base resin to satisfy all properties required for a hair fixative, such as stiffness, feel, combability and anti-flaking property.

Then, an application of an anionic urethane resin as a base resin for a hair fixative is proposed as seen in Japanese Provisional Publication TOKKAIHEI 6-321741. When such an anionic urethane resin is used, a hair fixative having good stiffness, feel and anti-flaking property, which are inconsistent to each other, can be prepared. In this viewpoint, a hair fixative using such an anionic urethane resin is superior to a hair fixative using the above mentioned acrylic resin. However, when the anionic urethane resin is used, a problem of inferior shampoo removability may be caused.

Accordingly, it is an object of the present invention to provide a cosmetic resin composition for preparation of a hair fixative having all the properties of stiffness, shampoo removability, feel, gloss, combability and anti-flaking property and to provide a cosmetic using such a cosmetic resin composition.

In accordance with a first aspect of the present invention to achieve the object described above, there is provided a cosmetic resin composition consisting essentially of an amphoteric urethane resin having a carboxyl group and a tertiary amino group in one molecule thereof, the amphoteric urethane resin having polysiloxane linkage in its structure. In accordance with a second aspect of the present invention, there is provided cosmetics using the cosmetic resin composition.

The inventors of the present invention found that a hair fixative having stiffness, feel, combability, anti-flaking property and the like can be obtained by using an amphoteric urethane resin having a carboxyl group and a tertiary amino group in one molecule thereof as a base resin and filed a patent application about a resin composition consisting essentially of the amphoteric urethane resin Japanese Patent Application No. TOKUGANHEI 10-27595). Improvement in each property when using the amphoteric resin is due to the following reason. That is, using the urethane resin as a main skeleton of a base resin makes it possible that stiffness is compatible with feel, combability and anti-flaking property, which are originally contrary to each other, due to elasticity and toughness of the urethane resin. Further, by using the amphoteric urethane resin having a carboxyl group and a tertiary amino group, it becomes possible to prepare a hair fixative superior in waterproof against neutral water because the carboxyl group and the tertiary amino group are ion-bonded, and also superior in shampoo removability because the ion-bond is cut by shampoo. In addition, since the amphoteric urethane resin has a cationic tertiary amino group, which interacts with a negatively charged hair surface, in its molecular chains, better adhesion can be obtained compared with a conventional anionic urethane resin.

Thus, in the case where the amphoteric urethane resin is used as a base resin, shampoo removability can be improved compared with the case where the conventional anionic urethane resin is used. However, to obtain sufficient shampoo removability, there are compositional restrictions, to some degree, such as adjustment of molecular weight of the amphoteric urethane resin, choice of urethane skeleton or the like, which may be a defect of low degree of freedom in designing physical properties, such as hardness, flexibility or the like, important for polymer to be used for a hair fixative. Then, the inventors further made researches about the resin composition consisting essentially of the amphoteric urethane resin. As a result, it was found that further improvement in shampoo removability can be obtained by the amphoteric urethane resin even with a higher molecular weight or a low glass transition temperature by introducing a structural unit derived from an ethylene oxide in the structure of the amphoteric urethane resin as nonionic hydrophilic component, and hardness and elasticity of the base resin which contribute to feel or stiffness required for a hair fixative, can be widely controlled. Thus, the inventors have attained the present invention.

The present invention will hereinafter be described by way of embodiments thereof.

The cosmetic resin composition of the present invention consists essentially of an amphoteric resin having a carboxyl group and a tertiary amino group in one molecule thereof. The most characteristic point of the present invention is that the amphoteric urethane resin has a structural unit derived from an ethylene oxide in its structure. In addition, the phrase "consisting essentially of an amphoteric urethane resin" means generally preparation of the cosmetic resin composition of interest by adding other components into the amphoteric urethane resin, however, includes the case where the cosmetic resin composition consists only of the amphoteric urethane resin.

The above-mentioned amphoteric urethane resin having a structural unit derived from an ethylene oxide may be obtained, for example, by reacting a polyol compound [component (A)], a polyisocyanate compound [component (B)], a polyethylene oxide derivative [component (C)] having an active hydrogen and a compound [component (D)] having an active hydrogen and a carboxyl group with each other in excess of isocyanate groups so as to produce a prepolymer containing an isocyanate group and reacting the prepolymer with a compound [component (E)] having an active hydrogen and a tertiary amino group. Alternatively, the amphoteric urethane resin having a structural unit derived from an ethylene oxide may be obtained by changing the reaction order of the component (D) for the component (E) in excess of isocyanate groups so as to produce a prepolymer containing an isocyanate group and reacting the prepolymer with the component (D). The amphoteric urethane resin of interest can be produced more easily and more safely by such methods than the conventional method. In addition, if both the component (D) and the component (E) are simultaneously reacted together with the components (A) to (C) In the above methods, a carboxyl group of the component (D) and a tertiary amino group of the component (E) initially form a salt which becomes insoluble to the reaction system and a reaction with the isocyanate compound may not occur even in the presence of an OH group. As a result, the amphoteric urethane resin of interest cannot be produced. That is, as above mentioned, the amphoteric urethane resin having a structural unit derived from an ethylene oxide can be produced by firstly reacting one of the component (D) and the component (E) together with the components (A) to (C) and then reacting the other component (D) or (E).

The polyol compound of the component (A) is not specifically limited, but any of the polyol compounds generally used for producing polyurethane. Examples of the polyol compound include polyester polyol, polyether polyol, polycarbonate polyol, polybutadiene polyol, polyisoprene polyol, polyolefin polyol, polyacrylic ester polyol. These may be used either alone or in combination thereof. Among all, polyester polyol and polyether polyol are especially preferred. Examples of the polyester polyol include products obtained by condensation polymerizing at least one of dicarboxylic acids such as succinic acid, glutaric acid, adipic acid, sebacic acid, azelaic acid, maleic acid, fumaric acid, phthalic acid, terephthalic acid and the like with at least one of polyhydric alcohols such as ethylene glycol, propylene glycol, 1,4-butanediol, 1,3-butanediol, 1,6-hexanediol, neopentyl glycol, 1,8-octanediol, 1,10-decanediol, diethylene glycol, spiroglycol, trimethylolpropane and thelike, and products obtained by ring-opening addition polymerizing cyclic ethers such as ethylene oxide, propylene oxide oxetane and tetrahydrofuran into water, polyol, phenols such as bisphenol A, hydrogenated phenols, primary amines and secondary amines. Examples of such products include polyoxyethylene polyol, polyoxypropylene polyol, polyoxytetramethylene polyol and products (either a blocked copolymer or a random copolymer in case of a copolymer) obtained by ring-opening polymerizing lactones. Further, examples of polyether polyol may be obtained by ring-opening addition polymerizing cyclic ethers such as ethylene oxide, propylene oxide oxetane and tetrahydrofuran into water, polyhydric alcohols for synthesizing the polyester polyol, phenols such as bisphenol A, hydrogenated phenols, primary amines and secondary amines. Examples of such products include polyoxyethylene polyol, polyoxypropylene polyol, polyoxytetramethylene polyol and products (either a blocked copolymer or a random copolymer in case of a copolymer) obtained by ring-opening addition polymerizing at least one of propylene oxide and ethylene oxide into bisphenol A.

The polyisocyanate compound of the component (B) is not specifically limited. Examples thereof include organic diisocyanate compounds such as aliphatic diisocyanate compounds, alicyclic diisocyanate compounds and aromatic diisocyanate compounds. These may be used either alone or in combination thereof. Examples of the aliphatic diisocyanate compounds include ethylene diisocyanate, 2,2,4-trimethyl hexamethylene diisocyanate, 1,6-hexamethylene diisocyanate. Examples of the alicyclic diisocyanate compounds include hydrogenated diphenyl methane-4,4'-diisocyanate, 1,4-cyclohexane diisocyanate methylcyclohexylene diisocyanate, isophorone diisocyanate, norbornane diisocyanate. Examples of the aromatic diisocyanate compounds include diphenyl methane-4,4'-diisocyanate, xylylene diisocyanate, toluene diisocyanate and naphthalene diisocyanate. Among all, 1,6-hexamethylene diisocyanate, isophorone diisocyanate, norbornane diisocyanate and the like are preferred in viewpoints of the performance cost.

The specific polyethylene oxide derivative of the component (C) is not specifically limited, but any of compound wherein a structural unit derived from an ethylene oxide (abbreviated to "EO", hereinafter) can be introduced into the structure of the amphoteric urethane resin, may be used. The structural unit derived from the EO introduced into the structure of the amphoteric urethane resin includes an EO unit represented by the following general formula (1) and a propylene oxide (abbreviated to "PO", hereinafter) unit represented by the following general formula (2), among which the EO unit is preferred. The amphoteric urethane resin may have both of the EO unit and the PO unit. The ratio of the EO unit and the PO unit is preferably within a range of EO unit/PO unit=10/0 to 2/8 on a weight basis, more preferably EO unit/PO unit=10/0 to 4/6.

A repetitive number 'n' of the EO unit in the above general formula (1) is preferably within a range of n=3 to 300, more preferably n=20 to 120. When the number 'n' is less than 3, the amount of the EO unit introduced into the amphoteric urethane resin is too small, so that sufficient hydrophilic property cannot be imparted, thereby sufficient shampoo removability may not be obtained. On the other hand, when the number 'n' exceeds 300, the hydrophilic property of the amphoteric urethane resin itself becomes too strong so as to have bad effects on moisture resistance and the like. Also, a repetitive number 'm' of the PO unit in the above general formula (2) is preferably within the same range as the above EO unit. In addition, when having both the EO unit and the PO unit, it is preferred that a total amount of 'n' and 'm' is within the above range. That is, the total amount is within a range of n+m=3 to 300, more preferably n+m=20 to 120.

Examples of the polyethylene oxide derivative [component (C)] include polyoxyethylene glycol (PEG) and polyoxyethylene polyoxypropylene glycol (EOPO blocked copolymer), among which polyoxyethylene glycol is preferred. The above polyethylene oxide derivative [component (C)] may be either of a type having OH groups at both terminals, a type having $NH_2$ groups at both terminals, a type having an OH group at one terminal and a type having an $NH_2$ at one terminal. When the type having OH groups at both terminals is used, the amphoteric urethane resin having the EO unit as a main chain can be obtained. When the type having an OH group at one terminal or the type having an $NH_2$ at one terminal is used, the amphoteric urethane resin having the EO unit as a side chain or at a terminal can be obtained.

The above specific polyethylene oxide derivative [component (C)] has preferably a molecular weight of 200 to 20,000, more preferably 2,000 to 10,000.

The compound [component (D)] having an active hydrogen and a carboxyl group is not specifically limited, but any of compound which may have at least one active hydrogen and at least one carboxyl group in its molecule. Examples include dimethylol propionic acid (DMPA), dimethylol butanoic acid and polycaprolactone diol having a carboxyl group. These may be used either alone or in combination thereof.

The compound [component (E)] having an active hydrogen and a tertiary amino group is not specifically limited, but any of compound which may have at least one active hydrogen and at least one tertiary amino group in its molecule. Examples include N-alklyldialkanolamine compound such as N-methyldiethanol-amine, and dimethylaminoethanol. These may be used either alone or in combination thereof.

In preparation of the prepolymer containing an isocyanate group by using each of the above components, it is preferred to use a chain extender. The use of the chain extender makes it possible to adjust various properties of the obtained amphoteric urethane resin as a final product. The chain extender is not specifically limited. Examples include low molecular weight polyols and amines.

In preparation of the amphoteric urethane resin, solvents may be used, as required. For example, it is especially preferred to use solvents which may solve both a raw material and the obtained polyurethane. Examples include amides such as N-methyl pyrrolidone, dimethylformamide and dimethylacetamide, ketones such as acetone and methyl ethyl ketone and esters such as ethyl acetate as well as cellosolve acetate and cellosolve ether. In addition, in preparation of the amphoteric urethane resin, a polymerization catalyst conventionally known in the field of polyurethane may be used. Examples include tertiary amine catalyst and organometallic catalyst. As the tertiary amine catalyst, [2,2,21] diazabicyclo octane (DABCO), tetramethylene diamine, N-methylmorpholine, diazbicyclo undecene (DBU) may be used. As the organometallic catalyst, examples include dibutyltindilaurate.

It is preferred that the ratio of the carboxyl group and the tertiary amino group (the ratio of the numbers of both groups) in the amphoteric urethane resin obtained by using each of the above components is the carboxilic group/the tertiary group=1/10 to 10/1. That is, when the ratio is within the above range, excellent washability may be imparted.

In addition, any other ingredients generally used in cosmetics other than the specific amphoteric urethane resin, such as pigment, coloring matter, colorant, fragrance, surfactant, moisturizer, preservative, antiseptic, disinfectant and antioxidant may be added to the cosmetic resin composition.

The cosmetic resin composition of the present invention is used for, for example, hair fixatives such as a mousse hair fixative, a gel hair fixative, a spray hair fixative and a pump spray hair fixative, a conditioning shaving cream agent, a film forming agent such as skin care lotion, foundation, eye liner and manicure, and viscosity adjuster. Especially, the cosmetic resin composition is useful for a hair fixative.

It is preferred that the specific amphoteric urethane resin is applied for the above usage after being dispersed as a dispersion by dispersing thereof into water or being solubilized as an aqueous solution by solubilizing thereof into water, respectively. In this case, it is preferred that the amphoteric urethane resin is dispersed into water containing aliphatic polyamine. That is, when the polymer is reacted with the aliphatic polyamine as the polymer is dispersed into water by controlling polymerization in excess of isocyanate groups, NH groups and $NH_2$ groups of the aliphatic polyamide rapidly react with the isocyanate groups to generate urea bonds in water, resulting in acceleration of polymerization. The aliphatic polyamine is not specifically limited. Examples include triethylamine, ethylene diamine, propylene diamine, piperazine and diethlylene triamine. Further, it is possible that silane coupling agent may be added into the dispersion of the amphoteric urethane resin for improvement of adhesive property with other base materials. Still further, various additives such as a protective colloid agent, an antibacterial agent and an antifungal agent may be added to give preservation stability.

Examples will next be described along with Comparative Examples.

EXAMPLE 1

70 g of isophorone diisocyanate (IPDI), 80 g of diethylene glycol adipate (DEGA, molecular weight 2,000), 20 g of an adduct of bisphenol A with ethylene oxide (Newpol BP3P, available from Sanyo Chemical industries Ltd., molecular weight 400, repetitive numbers of the EO unit, n+n=3), 26 g of polyoxyethylene glycol (PEG, molecular weight 2,000, a repetitive number of the EO unit, n=50) and 16.9 g of dimethylol propionic acid (DMPA) were put into a four-neck flask provided with a stirrer, a thermometer, an inlet tube for nitrogen and a reflux condenser. Then, 50 g of ethyl acetate as a solvent and 0.02 g of dibutyltindilaurate (DBTDL) as a catalyst were added thereto, warmed to 80 by an oil bath to be allowed to react for 4 hours. Thereafter, 5.6 g of N-methyldiethanolamine (NMDETA) and 60 g of ethyl acetate were added thereto and allowed to react at 80 for 2 hours, for obtaining polyurethane prepolymer solution wherein NCO groups remain. After thus obtained polyurethane prepolymer wherein the NCO groups remain was cooled down to 50, 600 g of water containing 12.7 g of triethylamine and 3.3 g of diethanolamine was added thereto under high-speed agitation to be dispersed, and then polymerized by chain-lengthening reaction at 50 for 3 hours. The ethyl acetate was withdrawn from thus obtained dispersion and an amphoteric urethane resin dispersion substantially not including a solvent and having an ethylene oxide chain in its structure was obtained.

EXAMPLE 2

70 g of isophorone diisocyanate (IPDI), 70 g of diethylene glycol adipate (DEGA, molecular weight 2,000), 26 g of polyoxyethylene glycol (PEG, molecular weight 2,000, a repetitive number of the EO unit, n=50) and 16.9 g of dimethylol propionic acid (DMPA) were put into a four-neck flask provided with a stirrer, a thermometer, an inlet tube for nitrogen and a reflux condenser. Then, 50 g of ethyl acetate as a solvent and 0.02 g of dibutyltindilaurate (DBTDL) as a catalyst were added thereto, warmed to 80 by an oil bath to be allowed to react for 4 hours. Thereafter, 5.6 g of N-methyldiethanolamine (NMDEtA) and 60 g of ethyl acetate were added thereto and allowed to react at 80 for 2 hours, for obtaining polyurethane prepolymer solution wherein NCO groups remain was cooled down to 50, 600 9 of water containing 12.7 g of triethylamine and 3.3 g of diethanolamine was added thereto under high-speed agitation to be dispersed, and then polymerized by chain-lengthening reaction at 50 for 3 hours. The ethyl acetate was withdrawn from thus obtained dispersion and an amphoteric urethane resin dispersion substantially not including solvent and having an ethylene oxide chain in its structure was obtained.

EXAMPLE 3

70 g of isophorone diisocyanate (IPDI), 80 g of diethylene glycol adipate (DEGA, molecular weight 2,000), 10 g of an adduct of bisphenol A with ethylene oxide (Newpol BP3P, available from Sanyo Chemical industries Ltd., molecular weight 400, repetitive numbers of the EO unit, n+n=3), 11 g of polyoxyethylene glycol (PEG, molecular weight 200, a repetitive number of the EO unit, n=250) and 16.9 g of dimethylol propionic acid (DMPA) were put into a four-neck flask provided with a stirrer, a thermometer, an inlet tube for nitrogen and a reflux condenser. Then, 50 g of ethyl acetate as a solvent and 0.02 g of dibutyltindilaurate (DBTDL) as a catalyst were added thereto, warmed to 80 by an oil bath to be allowed to react for 4 hours. Thereafter, 5.6 g of N-methyldiethanolamine (NMDETA) and 60 g of ethyl acetate were added thereto and allowed to react at 80 for 2 hours, for obtaining polyurethane prepolymer solution where NCO groups remain. After thus obtained polyurethane prepolymer wherein the NCO groups remain was cooled down to 50, 600 g of water containing 12.7 g of triethylamine and 3.3 g of diethanolamine was added thereto under high-speed agitation to be dispersed, and then polymerized by chain-lengthening reaction at 50 for 3 hours. The ethyl acetate was withdrawn from thus obtained dispersion and an amphoteric urethane resin dispersion substantially not including an organic solvent and having a ethylene oxide chain in its structure was obtained.

EXAMPLE 4

70 g of isophorone diisocyanate (IPDI), 80 g of diethylene glycol adipate (DEGA, molecular weight 2,000), 20 g of an adduct of bisphenol A with ethylene oxide (Newpol BP3P available from Sanyo Chemical industries, Ltd., molecular weight 400, repetitive numbers of the EO unit, n+n=3), 52 g of polyoxyethylene glycol (PEG, molecular weight 10,000, a repetitive number of the EO unit, n=250) and 16.9 g of dimethylol propionic acid (DMPA) were put into a four-neck flask provided with a stirrer, a thermometer, an inlet tube for nitrogen and a reflux condenser. Then, 50 g of ethyl acetate as a solvent and 0.02 g of dibutyltindilaurate (DBTDL) as a catalyst were added thereto, warmed to 80 by an oil bath to be allowed to react for 4 hours. Thereafter, 5.6 g of N-methyldiethanolamine (NMDEtA) and 60 g of ethyl acetate were added thereto and allowed to react at 80 for 2 hours, for obtaining polyurethane prepolymer solution wherein NCO groups remain. After thus obtained polyurethane prepolymer wherein the NCO groups remain was cooled down to 50, 600 g of water containing 12.7 g of triethylamine and 3.3 g of diethanolamine was added thereto under high-speed agitation to be dispersed, and then polymerized by chain-lengthening reaction at 50 for 3 hours. The ethyl acetate was withdrawn from thus obtained dispersion and an amphoteric urethane resin dispersion substantially not including a solvent and having an ethylene oxide chain in its structure was obtained.

EXAMPLE 5

70 g of isophorone diisocyanate (IPDI), 80 g of diethylene glycol adipate (DEGA, molecular weight 2,000), 20 g of an adduct of bisphenol A with ethylene oxide (Newpol BP3P available from Sanyo Chemical industries, Ltd., molecular weight 400, repetitive numbers of the EO unit, n+n=3), 26 g of polyoxypropylene glycol (EOPO blocked copolymer, molecular weight 2,000, a repetitive number of the EO unit, n=20, a repetitive number of the PO unit, m=21) and 16.9 g of dimethylol propionic acid (DMPA) were put into a four-neck flask provided with a stirrer, a thermometer, an inlet tube for nitrogen and a reflux condenser. Then, 50 g of ethyl acetate as a solvent and 0.02 g of dibutuyltindilaurate (DBTDL) as a catalyst were added thereto, warmed to 80 by an oil bath to be allowed to react for 4 hours. Thereafter, 5.6 g of N-methyldiethanolamine (NMDETA) and 60 g of ethyl acetate were added thereto and allowed to react at 80 for 2 hours, for obtaining polyurethane prepolymer solution wherein NCO groups remain. After thus obtained polyurethane prepolymer wherein the NCO groups remain was cooled down to 50, 600 g of water containing 12.7 g of triethylamine and 3.3 g of diethanolamine was added thereto under high-speed agitation to be dispersed, and then polymerized by chain-lengthening reaction at 50 for 3 hours. The ethyl acetate was withdrawn from thus obtained dispersion and an amphoteric urethane resin dispersion substantially not including a solvent and having an ethylene oxide chain in its structure was obtained.

EXAMPLE 6

70 g of isophorone diisocyanate (IPDI), 80 g of diethylene glycol adipate (DEGA, molecular weight 2,000), 20 9 of an adduct of bisphenol A with ethylene oxide (Newpol BP3P available from Sanyo Chemical industries Ltd., molecular weight 400, repetitive numbers of the EO unit, n=50), and 16.9 g of dimethylol propionic acid (DMPA) were put into a four-neck flask provided with a stirrer, a thermometer, an inlet tube for nitrogen and a reflux condenser. Then, 50 g of ethyl acetate as a solvent and 0.02 g of dibutyltindilaurate (DBTDL) as a catalyst were added thereto, warmed to 80 by an oil bath to be allowed to react for 4 hours. Thereafter, 5.6 g of N-methyldiethanolamine (NMDETA) and 60 g of ethyl acetate were added thereto and allowed to react at 80 for 2 hours, for obtaining polyurethane prepolymer solution wherein NCO groups remain. After thus obtained polyurethane prepolymer wherein the NCO groups remain was cooled down to 50, 600 g of water containing 12.7 g of triethylamine and 3.3 g of diethanolamine was added thereto under high-speed agitation to be dispersed, and then polymerized by chain-lengthening reaction at 50 for 3 hours. The ethyl acetate was withdrawn from thus obtained dispersion and an amphoteric urethane resin dispersion substantially not including a solvent and having an ethylene oxide chain (at a terminal) in its structure was obtained.

COMPARATIVE EXAMPLE 1

70 g of isophorone diisocyanate (IPDI), 106 g of diethylene glycol adipate (DEGA, molecular weight 2,000), 20 g of an adduct of bisphenol A with ethylene oxide (Newpol BP3P available from Sanyo Chemical industries, Ltd., molecular weight 400, repetitive numbers of the EO unit, n+n=3) and 16.9 g of dimethylol propionic acid (DMPA) were put into a four-neck flask provided with a stirrer, a thermometer, an inlet tube for nitrogen and a reflux condenser. Then, 50 g of ethyl acetate as a solvent and 0.02 g of dibutyltindilaurate (DBTDL) as a catalyst were added thereto, warmed to 80 by an oil bath to be allowed to react for 4 hours. Thereafter, 5.6 g of N-methyldiethanolamine (NMDETA) and 60 g of ethyl acetate were added thereto and allowed to react at 80 for 2 hours, for obtaining polyurethane prepolymer solution wherein NCO groups remain. After thus obtained polyurethane prepolymer wherein the NCO groups remain was cooled down to 50, 600 g of water containing 12.7 g of triethylamine and 3.3 g of diethanolamine was added thereto under high-speed agitation to be dispersed, and then polymerized by chain-lengthening reaction at 50 for 3 hours. The ethyl acetate was withdrawn from thus obtained dispersion and an amphoteric urethane resin dispersion substantially not including a solvent was obtained.

COMPARATIVE EXAMPLE 2

70 g of isophorone diisocyanate (IPDI), 106 g of diethylene glycol adipate (DEGA, molecular weight 2,000), 20 g of an adduct of bisphenol A with ethylene oxide (Newpol BP3P available from Sanyo Chemical industries, Ltd., molecular weight 400, repetitive numbers of the EO unit, n+n=3) and 16.9 g of dimethylol propionic acid (DMPA) were put into a four-neck flask provided with a stirrer, a thermometer, an inlet tube for nitrogen and a reflux condenser. Teen, 50 g of ethyl acetate as a solvent and 0.02 g of dibutyltindilaurate (DBTDL) as a catalyst were added thereto, warmed to 80 by an oil bath to be allowed to react for 6 hours, for obtaining polyurethane prepolymer solution wherein NCO groups remain. After thus obtained polyurethane prepolymer wherein the NCO groups remain was cooled down to 50, 600 g of water containing 12.7 g of triethylamine and 3.3 g of diethanolamine was added thereto under high-speed agitation to be dispersed, and then polymerized by chain-lengthening reaction at 50 for 3 hours. The ethyl acetate was withdrawn from thus obtained dispersion and an amphoteric urethane resin dispersion substantially not including a solvent was obtained.

COMPARATIVE EXAMPLE 3

70 g of isophorone diisocyanate (IPDI), 80 g of diethylene glycol adipate (DEGA, molecular weight 2,000), 20 g of an adduct of bisphenol A with ethylene oxide (Newpol BP3P available from Sanyo Chemical industries, Ltd., molecular weight 400, repetitive numbers of the EO unit, n=50) and 16.9 g of dimethylol propionic acid (DMPA) were put into a four-neck flask provided with a stirrer, a thermometer, an inlet tube for nitrogen and a reflux condenser. Then, 50 g of ethyl acetate as a solvent and 0.02 g of dibutyltindilaurate (DBTDL) as a catalyst were added thereto, warmed to 80 by an oil bath to be allowed to react for 6 hours, for obtaining polyurethane prepolymer solution wherein NCO groups remain. After thus obtained polyurethane prepolymer wherein the NCO groups remain was cooled down to 50, 600 g of water containing 12.7 g of triethylamine and 3.3 g of diethanolamine was added thereto under high-speed agitation to be dispersed, and then polymerized by chain-lengthening reaction at 50 for 3 hours. The ethyl acetate was withdrawn from thus obtained dispersion and an amphoteric urethane resin dispersion substantially not including a solvent was obtained.

Mousse hair fixatives a to i were prepared by using thus obtained dispersions of Examples and Comparative Examples at mixing ratios as follows.

A Mousse Hair Fixative a

Ingredients shown in the following Table 1 were blended at proportions shown in the same table, and mixed until thus obtained mixture became homogenous, for obtaining X component. Then, Y component shown in the same table was added into the X component, for obtaining a mousse hair fixative a.

TABLE 1

| a mousse hair fixative a | (weight %) |
|---|---|
| X component | |
| the dispersion obtained by Example 1 | 3.0 (dry weight) |
| deionized water | 77.7 |
| polyoxyethylene stearyl ether *1 | 0.5 |
| ethanol | 10.0 |
| coconut oil fatty acid diethanolamide *2 | 0.8 |
| Y component | |
| propellant (LPG) | 8.0 |

*1: NIKKOL BS-20 available from Nikko Chemicals Co., Ltd.
*2: Amicor CDE-1, available from Mlyoshi Oil.

Instead of the dispersion obtained by Example 1 for the X component shown in the Table 1, each dispersion of Examples 2, 3, 4, 5 and 6 was used. Except for that, mousse hair fixatives b, c, d, e and f were prepared in the same way as the mousse hair fixative a.

Mousse Hair Fixatives g, h and i

Instead of the dispersion obtained by Example 1 shown in the Table 1, each dispersion of Comparative Examples 1, 2 and 3 was used. Except for that, mousse hair fixatives g, h and i were prepared in the same way as the mousse hair fixative a.

"Curl retention" and "shampoo removability" of thus obtained mousse hair fixatives a to i were determined in accordance with the following standards therefore. The results are shown in the following Table 2.

Curl Retention

Each 0.6 g of the thus obtained mousse hair fixatives was applied on a separate hair swatch of black virgin hair (15 cm in length, 3 9 in weight), respectively, and each 5 swatches per each of Examples and Comparative Examples were prepared and were dried at 50 overnight. Next, the dried swatches were suspended on graduated boards and were put into a thermo-hydrostat where temperature was 30 and humidity was 90% RH. Each length (a) of the initial curls and each length (b) of the curls after 5 hours were measured and each curl retention was evaluated in accordance with the following formula. As the curl retention is nearer to 100%, it shows that the curl retention is stronger. In the formula 1, L is a length of the swatch fully extended.

$$\text{Curl retention}(\%) = \{(L-b)/(L-a)\} \times 100 \qquad \text{Formula 1}$$

Shampoo Removability

Each 0.6 9 of the thus obtained mousse hair fixatives was applied on a separate hair swatch of black virgin black (15 cm in length, 3 g in weight), respectively, and the hair swatch was dried at room temperature, for obtaining each hair-dressed swatch. After each swatch was slightly loosened in warm water of 40 for 30 seconds, 0.4 g of 10% shampoo solution was applied thereon and washed for 30 seconds. Thereafter, each swatch was rinsed in warm water of 40 so as to be washed out, and then dried sufficiently at 50. Thus obtained swatch was evaluated for stiffness. In the evaluation, indicates that the dried swatch had no stiffness due to excellent shampoo removability, indicates that the dried swatch had substantially no stiffness due to good shampoo removability and indicates insufficient shampoo removability.

Also, feel, stiffness, gloss, tactile property, combability and anti-flaking property of the thus obtained mousse hair fixatives a to i were evaluated. Each 0.8 g of the thus obtained mousse hair fixatives was applied on a separate hair swatch of black virgin hair (25 cm in length, 5.0 g in weight), respectively, and the hair swatch was dried at room temperature. The hair swatch was determined in accordance with the following standards therefore. The results are also shown in the following Table 2.

Feel

Indicates that no hair dishevelment was caused on a swatch after being dried and elasticity was excellent, indicates that elasticity was good and indicates that feel was slightly inferior.

Stiffness

Indicates that no hair dishevelment was caused on a swatch after being dried and stiffness was excellent, indicates that stiffness was good and indicates that stiffness was slightly inferior.

Combability

Indicates that combability of a swatch after being dried was excellent, indicates that combability is good, indicates that combability is slightly inferior and X indicates that combability is inferior.

Anti-flaking Property

Indicates that no flake was caused on a swatch after being dried with 10-time combing, indicates that almost no flake caused and indicates that slightly flake caused.

TABLE 2

| | mousse hair fixatives | | | | | | | | |
|---|---|---|---|---|---|---|---|---|---|
| | a | b | c | d | e | f | g | h | l |
| Curl retention (%) | 90 | 95 | 90 | 90 | 95 | 90 | 90 | 90 | 90 |
| Shampoo removability | | | | | | | | | |
| Feel | | | | | | | | | |
| Stiffness | | | | | | | | | |
| Combability | | | | | | | | x | |
| anti-flaking property | | | | | | | | | |

From results of Table 2, it is found that mousse hair fixatives a to f are superior in all properties of curl retention, shampoo removability, feel, stiffness, combability and anti-flaking property. Also, it is found that mousse hair fixatives a to f are especially excellent in shampoo removability and feel because they use an amphoteric urethane resin having the EO unit in its structure.

On the other hand, it is found that a mousse hair fixative g is superior to a mousse hair fixative h, which uses an anionic urethane resin, in shampoo removability, stiffness and combability, because the mousse hair fixative g uses the amphoteric urethane resin. However, the hair fixative g is inferior to hair fixatives a to f, having the EO unit in the structure of the amphoteric urethane resin. In addition, a mousse hair fixative h is remarkably inferior in combability because the mousse hair fixative h uses an anionic urethane resin, and is also inferior in other properties except for feel. A mousse hair fixative i contains the urethane resin which, though having the EO unit in the structure thereof, is not amphoteric but anionic. Therefore, it is found that the mousse hair fixative i is inferior in shampoo removability, feel, combability and anti-flaking property to mousse hair fixatives a to f containing the amphoteric urethane resin having the EO unit in the structure thereof.

Next, gel hair fixatives a to i were prepared using each dispersion of Examples and Comparative Examples in accordance with the following proportions.

Gel Hair Fixatives a

Ingredients shown in the following Table 3 were blended in proportions shown in the same table and mixed until a viscous gel was formed, for obtaining X component. Next, ingredients shown in Table 3 were blended in proportions shown in the same table, for obtaining Y component Thus obtained Y component was added into thus obtained X component and mixed until it became homogeneous, for obtaining a gel hair fixative a.

TABLE 3

| gel hair fixative a | (weight %) |
|---|---|
| X component | |
| Thickener* | 1.5 (dry weight) |
| Triethanolamine | 1.1 |

TABLE 3-continued

| gel hair fixative a | (weight %) |
|---|---|
| Ethanol | 10.0 |
| Deionized water | 50.0 |
| Y component | |
| the dispersion of Example 1 | 3.0 (dry weight) |
| Deionized water | 34.4 |

*Structure 2001 available from National Starch and Chemical Company.

Gel Hair Fixatives b, c, d, e and f

Instead of the dispersion of Example 1 for Y component shown in the above Table 3, each dispersion of Examples 2, 3, 4, 5 and 6 was used. Except for that, gel hair fixatives b, c, d, e and f were prepared in the same way as the gel hair fixative a.

Gel Hair Fixatives g, h and i.

Instead of the dispersion of Example 1 for Y component shown in the above Table 3, each dispersion of Comparative Examples 1, 2 and 3 was used. Except for that, gel hair fixatives g, h and i were prepared in the same way as the gel hair fixative a.

Curl retention, shampoo removability, feel, stiffness, combability and anti-flaking property of thus obtained gel hair fixatives a to i were determined in accordance with the above mentioned standards therefor. The generally same results were obtained as in the case where the mousse hair fixatives a to i were used.

In addition, spray hair fixatives a to i were prepared using the dispersions of Examples and comparative Examples at mixing ratios as follows.

Spray Hair Fixative a

Ingredients shown in the following Table 4 were blended in proportions shown in the same table and mixed until it became homogeneous, for obtaining X component. Next, ingredients shown in the Table 4 were blended in proportions shown in the same table, for obtaining Y component. Thus obtained Y component was added into the X component, for obtaining a spray hair fixative a.

TABLE 4

| Spray hair fixative a | (weight %) |
|---|---|
| X component | |
| The dispersion of EXAMPLE 1 | 3.0 (dry weight) |
| Deionized water | 7.0 |
| Dioctyl sodium sulfosuccinate* | 0.3 |
| Ethanol | 49.7 |
| Y component | |
| Propellant (LPG) | 40.0 |

*Monawet MO-70E available from Mona Industries Inc.

Spray Hair Fixatives b, c, d, e and f

Instead of the dispersion of Example 1 for X component shown in the above Table 4, each dispersion of Examples 2, 3, 4, 5 and 6 was used. Except for that, spray hair fixatives b, c, d, e and f were prepared in the same way as the spray hair fixative a.

Spray Hair Fixatives g, h and i

Instead of the dispersion of Example 1 for X component shown in the above Table 4, each dispersion of Comparative Examples 1, 2 and 3 was used. Except for that, spray hair fixatives g, h and i were prepared in the same way as the spray hair fixative a.

Curl retention, shampoo removability, feel, stiffness, combability and anti-flaking property of thus obtained spray hair fixatives a to i were determined in accordance with the above mentioned standards therefor. The generally same results were obtained as in the case where the mousse hair fixatives a to i were used.

In addition, pump spray hair fixatives a to i were prepared by using the dispersions of Examples and Comparative Examples at mixing ratios as follows.

Pump Spray Hair Fixative a

Ingredients shown in the following Table 5 were blended in proportions shown in the same table and mixed until it became homogenous, for obtaining a pump hair spray fixative a.

TABLE 5

| Pump spray hair fixative a | (weight %) |
| --- | --- |
| The dispersion of Example 1 | 3.0 (dry weight) |
| Dioctyl sodium sulfosuccinate* | 0.3 |
| Deionized water | 96.7 |

*Monawet MO-70E available from Mona Industries Inc.

Pump Spray Hair Fixatives b, c, d, e and f

Instead of the dispersion of Example 1 shown in the above Table 5, each dispersion of Examples 2, 3, 4, 5 and 6 was used. Except for that, pump spray hair fixatives b, c, d, e and f were prepared in the same way as the pump spray hair fixative a.

Pump Spray Hair Fixatives g, h and i

Instead of the dispersion of Example 1 shown in the above Table 5, each dispersion of Comparative Examples 1, 2 and 3 was used. Except for that, pump spray hair fixatives g, h and i were prepared in the same way as the pump spray hair fixative a.

Curl retention, shampoo removability, feel, stiffness, combability and anti-flaking property of thus obtained pump spray hair fixatives a to i were determined in accordance with the above mentioned standards therefor. The generally same results were obtained as in the case where the mousse hair fixatives a to i were used.

In addition, the cosmetic resin composition of the present invention may be used for a conditioning shaving cream agent, a film forming agent such as skin care lotion, emulsified foundation, cream foundation, eye liner and manicure, as mentioned below.

Conditioning Shaving Cream Agent

Ingredients sown in the following Table 6 were mixed in the proportions as shown in the same table and was warmed up to 80, for obtaining X component. Next, ingredients shown in the same table were mixed in the proportions shown in the same table and was warmed up to 80, for obtaining Y component. Then, the X component and the Y component were mixed at 80, the resulting mixture was cooled down to 40 and antiseptic and fragrance were added at each suitable amount, for obtaining the conditioning shaving cream agent of interest

TABLE 6

| | (weight %) |
| --- | --- |
| X component | |
| Stearic acid | 8.0 |
| Mineral oil | 2.0 |
| Isopropyl myristate | 2.0 |
| Glyceryl stearate | 0.5 |
| Y component | |
| Deionized water | 81.6 |
| Triethanolamine (99%) | 4.2 |
| The dispersion of Example 1 | 1.7 |

Skin Care Lotion

Ingredients shown in the following Table 7 were mixed in the proportions shown in the same table and was warmed up to 80, for obtaining X component. Next, ingredients shown in the same table were mixed in the proportions shown in the same table and was warmed up to 80, for obtaining Y component. Then, the X component and the Y component were mixed and agitated at 80 for 30 minutes. 20.00 weight % of 2% Carbopol 940 aqueous solution was added into the resulting mixture and agitated until it became homogenous. Thereafter, it was cooled down to 40, for obtaining the skin care lotion of interest.

TABLE 7

| | (weight %) |
| --- | --- |
| X component | |
| Methoxy octyl cinnamate | 7.50 |
| Polyoxy (PO) ether stearate | 1.00 |
| Emulsified glyceryl stearate | 1.00 |
| Stearic acid | 1.50 |
| A mixture of titanium dioxide and alkyl benzoate ($C_{12-15}$) | 1.70 |
| An adduct of dimethylcone with polyoxy ethylene (POE) | 0.50 |
| Y component | |
| Deionized water | 59.47 |
| Triethanolamine (99%) | 4.00 |
| The dispersion of Example 1 | 3.33 |
| Antiseptic | suitable amount |

Emulsified Foundation (1) Preparation of Pigment

Ingredients shown in the following Table 8 were mixed in proportions shown in the same table and the resulting mixture was pulverized by a grinding machine, for obtaining a pigment.

(2) Preparation of an Aqueous Phase

After deionized water was warmed to 70, bentonite was added thereto and was swollen. Then, a preliminarily prepared dispersion where sodium carboxymethylcellulose was dispersed into propylene glycol was added thereto to be solved. Further, triethanolamine and methylparaben were added thereto to be solved, for obtaining an aqueous phase.

(3) Preparation of an Oil Phase

After ingredients shown in the following Table 8 were mixed in proportions shown in the following table, the resulting mixture was warmed to 70 to 80 to be solved, for obtaining an oil phase.

(4) Preparation of a Pigment Dispersion

After the above pigment was added into the above aqueous phase with agitation, the resulting mixture was passed through a colloid mill, for obtaining a pigment dispersion.

(5) Emulsification

After the pigment dispersion and the oil phase were warmed to 75 and 80, respectively, the oil phase was added to the pigment dispersion with agitation. Then, the resulting mixture was cooled down, and fragrance was added thereto when temperature thereof was 45. The resulting mixture was further cooled with agitation down to room temperature, for obtaining the emulsified foundation of interest.

TABLE 8

|  | (weight %) |
| --- | --- |
| Oil phase | |
| Stearic acid | 2.4 |
| Propylene glycol monostearate | 2.0 |
| Cetostearyl alcohol | 0.2 |
| Liquid Ianoline | 2.0 |
| Liquid paraffin | 3.0 |
| Isopropyl myristate | 8.5 |
| Propylparaben | Suitable amount |
| Aqueous phase | |
| The dispersion of Example 1 | 1.0 |
| Deionized water | 63.1 |
| Sodium carboxymethylcellulose | 0.2 |
| Bentonite | 0.5 |
| Propylene glycol | 4.0 |
| Triethanol amine | 1.1 |
| Methylparaben | Suitable amount |
| Pigment | |
| Titanium oxide | 8.0 |
| Talc | 4.0 |
| Color pigment | Suitable amount |
| Fragrance | |
| Fragrance | Suitable amount |

Cream Foundation (1) Preparation of Pigment

Ingredients shown in the following Table 9 were mixed in proportions shown in the same table and the resulting mixture was pulverized by a grinding machine for obtaining a pigment.

(2) Preparation of an Aqueous Phase

Ingredients shown in the following Table 9 were mixed in proportions shown in the same table for obtaining an aqueous phase.

(3) Preparation of an Oil Phase

After ingredients shown in the following Table 9 were added in proportions shown in the same table, the resulting mixture was warmed to 70 to 80 to be solved, for obtaining an oil phase.

(4) Preparation of a Pigment Dispersion

After the above pigment was added into the above aqueous phase with agitation, the resulting mixture was passed through a colloid mill for obtaining a pigment dispersion.

(5) Emulsification

After the pigment dispersion and the oil phase were warmed to 75 and 80, respectively, the oil phase was added to the pigment dispersion with agitation. Then, the resulting mixture was cooled down, and fragrance was added thereto when temperature thereof was 50. The resulting mixture was further cooled with agitation down to room temperature, for obtaining the cream foundation of interest.

TABLE 9

|  | (weight %) |
| --- | --- |
| Oil phase | |
| Stearic acid | 5.0 |
| Lipophilic glycerin monostearate | 2.5 |
| Cetostearyl alcohol | 1.0 |
| Propylene glycol monolaurate | 3.0 |
| Liquid paraffin | 7.0 |
| Isopropyl myristate | 8.0 |
| Butylparaben | Suitable amount |
| Aqueous phase | |
| The dispersion of Example 1 | 1.0 |
| Deionized water | 52.3 |
| Triethanolamine | 1.2 |
| Sorbit | 3.0 |
| Methylparaben | Suitable amount |
| Pigment | |
| Titanium oxide | 8.0 |
| Kaoline | 5.0 |
| Talc | 2.0 |
| Bentnite | 1.0 |
| Color pigment | Suitable amount |
| Fragrance | |
| Fragrance | Suitable amount |

Eye Liner

After ingredients shown in the following Table 10 were mixed in proportions shown in the same table, the resulting mixture was warmed to 70 to 80 to be solved for obtaining an oil phase. Then, ingredients shown in Table 10 were mixed in proportions shown in the same table for obtaining an aqueous phase. Further, the warmed aqueous phase was added into the oil phase with agitation for emulsification. A preliminary swollen bentonite dispersion, pigment and fragrance were added in thus obtained emulsion. The resulting mixture was passed through a colloid mil to be dispersed and was cooled, for obtaining the eye liner of interest.

TABLE 10

|  | (weight %) |
| --- | --- |
| Oil phase | |
| Stearic acid | 3.5 |
| Bees wax | 2.0 |
| Carnauba wax | 0.5 |
| Microcrystalline wax | 5.0 |
| Aqueous phase | |
| The dispersion of Example 1 | 1.0 |
| Deionized water | 49.5 |
| Butylene glycol | 7.0 |
| Triethanolamine | 1.5 |
| Pigment | |
| pigment | 10.0 |
| Others | |
| 3% bentonite dispersion | 20.0 |
| Antiseptic | Suitable amount |
| Fragrance | Suitable amount |

Manicure

After pigment was dispersed in ion-exchanged water, the dispersion of Example 1 and other ingredients shown in the following Table 11 were added thereto in proportions shown in the same table. The resulting mixture was mixed with agitation until it became homogenous and was deaerated finally for obtaining the manicure of interest.

TABLE 11

|  | (weight %) |
| --- | --- |
| Aqueous phase | |
| The dispersion of Example 1 | 90 |
| Deionized water | 6.6 |
| Bentonite | 0.6 |
| Pigment | |
| Pigment | 2.5 |
| Others | |
| Fragrance | 0.1 |
| Antiseptic | 0.1 |
| A silicone antifoam agent | 0.1 |

Effect of the invention

As described above, the cosmetic resin composition of the present invention consists essentially of amphoteric urethane resin having a carboxyl group and a tertiary amino group in one molecule thereof. Thus, using urethane resin as a main skeleton of a base resin makes it possible due to elasticity and toughness of the urethane resin that stiffness is compatible with feel, combability and anti-flaking property, which are originally contrary to each other. Further, by using amphoteric urethane resin having a carboxyl group and a tertiary amino group, it becomes possible to prepare a hair fixative superior in waterproof against neutral water because the carboxyl group and the tertiary amino group are ion-bonded, and also superior in shampoo removability because the ion-bond is cut by shampoo. In addition, since the amphoteric urethane resin has a cationic tertiary amino group, which interacts with a negatively charged hair surface, in its molecular chain, better adhesion can be obtained compared with conventional anionic urethane resin. In addition, the amphoteric urethane resin, even though having a high molecular weight or a low glass transition temperature, further improves shampoo removability because it has a structural unit derived from an ethylene oxide therein as a nonionic hydrophilic component, and makes it possible to widely control hardness and elasticity of the base resin which contribute to feel or stiffness required for a hair fixative.

What is claimed:

1. A cosmetic resin composition consisting essentially of an amphoteric urethane resin having a carboxyl group and a tertiary amino group in one molecule thereof, the amphoteric urethane resin having a structural unit derived from an ethylene oxide in its structure, wherein the amphoteric urethane resin is obtained by reacting the following components (A) to (D) in excess of isocyanate groups so as to produce a prepolymer containing isocyanate groups and reacting the prepolymer with the following component (E);

(A) a polyol compound;

(B) a polyisocyanate compound;

(C) a polyethylene oxide derivative having an active hydrogen and from about 3 to about 300 ethylene oxide units;

(D) a compound having an active hydrogen and a carboxyl group;

(E) a compound having an active hydrogen and a tertiary amino group.

2. A cosmetic resin composition consisting essentially of an amphoteric urethane resin having a carboxyl group and a tertiary amino group in one molecule thereof, the amphoteric urethane resin having a structural unit derived from an ethylene oxide in its structure, wherein the amphoteric urethane resin is obtained by reacting the following components (A), (B), (C) and (E) in excess of isocyanate groups so as to produce a prepolymer containing isocyanate groups and reacting the prepolymer with the following (D);

(A) a polyol compound;

(B) a polyisocyanate compound;

(C) a polyethylene oxide derivative having an active hydrogen and from about 3 to about 300 ethylene oxide units;

(D) a compound having an active hydrogen and a carboxyl group;

(E) a compound having an active hydrogen and a tertiary amino group.

3. The cosmetic resin composition according to claim 1 or 2, wherein the cosmetic resin composition is for a hair fixative.

4. The cosmetic resin composition according to claim 1 or 2, wherein the amphoteric urethane resin is dispersed or solubilized into water.

5. A cosmetic using the cosmetic resin composition according to claim 4.

6. A cosmetic using the cosmetic resin composition according to claim 1 or 2.

7. The cosmetic according to claim 6, wherein the cosmetic is at least one selected from the group consisting of a mousse hair fixative, a gel hair fixative, a spray hair fixative, a pump spray hair fixative, a conditioning shaving cream agent and a film forming agent.

* * * * *

UNITED STATES PATENT AND TRADEMARK OFFICE
CERTIFICATE OF CORRECTION

PATENT NO.    : 6,692,729 B1
DATED         : February 17, 2004
INVENTOR(S)   : Seiji Asaoka et al.

It is certified that error appears in the above-identified patent and that said Letters Patent is hereby corrected as shown below:

Column 2,
Lines 47-49, replace the part of the sentence beginning with "...the amphoteric urethane resin having polysiloxane linkage in its structure." with -- the amphoteric urethane resin having a structural unit derived from an ethylene oxide in its structure. --

Signed and Sealed this

Fourth Day of January, 2005

JON W. DUDAS
*Director of the United States Patent and Trademark Office*